United States Patent [19]

Edwards et al.

[11] Patent Number: 5,346,477
[45] Date of Patent: Sep. 13, 1994

[54] PRESSURE GAUGE FOR REGULATING PRESSURE IN A DISPOSABLE PRESSURE CUFF

[75] Inventors: Floyd V. Edwards, Eggertsville; Norman M. Strobel, Newfane, both of N.Y.

[73] Assignee: Harmac Medical Products, Inc., Buffalo, N.Y.

[21] Appl. No.: 769,544

[22] Filed: Oct. 1, 1991

Related U.S. Application Data

[63] Continuation-in-part of Ser. No. 415,068, Sep. 29, 1989, Pat. No. 5,053,012.

[51] Int. Cl.$^5$ .................... A61M 37/00; A61M 1/00
[52] U.S. Cl. .................... 604/141; 604/142; 604/118; 604/185; 604/186; 604/246
[58] Field of Search ............ 604/65, 67, 118, 141–142, 604/145–147, 185–186, 246–250; 128/D12, D13; 137/505.41; 222/55, 61; 73/714, 715, 731, 146.8, 198, 199

[56] References Cited

U.S. PATENT DOCUMENTS

| | | | |
|---|---|---|---|
| 2,618,977 | 11/1952 | Hottenroth | 73/715 |
| 3,365,949 | 1/1968 | Robinson | 73/715 |
| 3,720,201 | 3/1973 | Ramsey, III | 73/731 |
| 4,267,833 | 5/1981 | Barger et al. | 604/250 |
| 4,432,468 | 2/1984 | Siff et al. | 604/65 |
| 4,507,116 | 3/1985 | Leibinsohn | 604/142 |
| 4,606,391 | 8/1986 | Achterholt | 73/146.8 |
| 4,690,514 | 5/1987 | Hinck et al. | 604/142 |
| 4,735,613 | 4/1988 | Bellin et al. | 604/142 |
| 5,053,011 | 10/1991 | Strobe et al. | 604/142 |
| 5,053,012 | 10/1991 | Edwards et al. | 604/146 |
| 5,147,310 | 9/1992 | Giannini et al. | 604/141 |
| 5,211,632 | 5/1993 | Tsukada | 604/246 |

FOREIGN PATENT DOCUMENTS

8805159  7/1988  World Int. Prop. O. ............ 73/199

*Primary Examiner*—Randall L. Green
*Assistant Examiner*—P. Zuttarelli
*Attorney, Agent, or Firm*—Woodcock Washburn Kurtz Mackiewicz & Norris

[57] ABSTRACT

Apparatus for regulating pressure in and for controllably pressurizing infusion devices includes a flow-through pressure gauge for indicating and regulating the pressures within such infusion devices between minimum and maximum desirable pressures. Such apparatus includes a gauge, coupled between a fluid source and the bladder portion of the pressure infusion device. The gauge receives pressurized fluid from the fluid source, provides fluid to the bladder, indicates a range of fluid pressures in the bladder and maintains the pressure of fluid in the bladder between minimum and maximum pressures. The gauge includes a telescopingly coupled member to indicate a range of pressures in the bladder. A first valve permits the passage of fluid through the gauge and into the bladder when the fluid pressure exceeds a minimum pressure. A second valve prevents the passage of fluid through the gauge and into the bladder when the fluid pressure exceeds a maximum pressure.

7 Claims, 6 Drawing Sheets

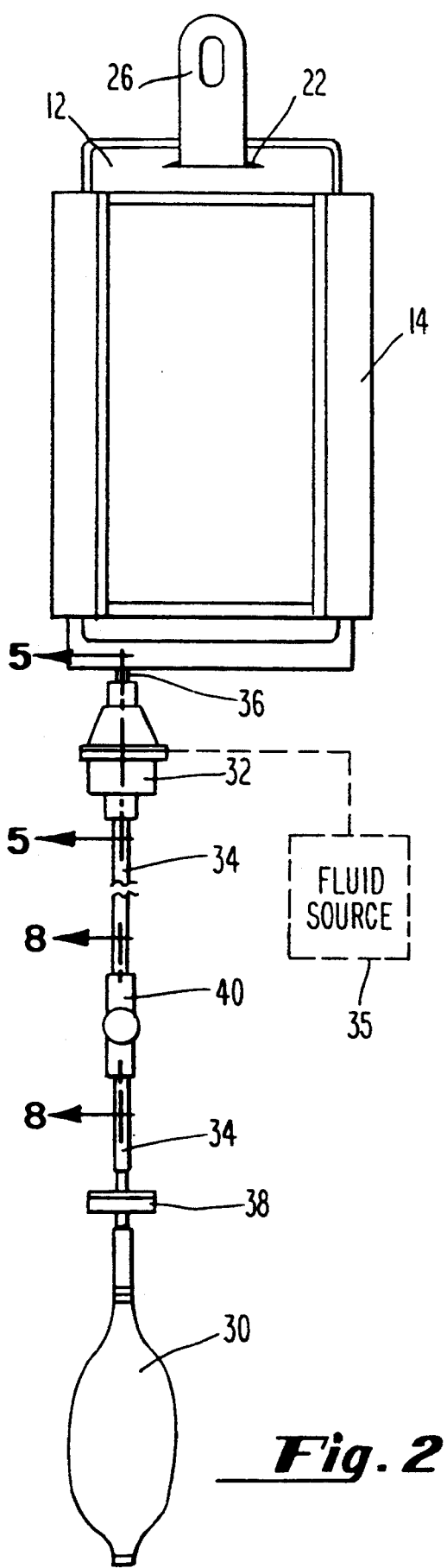
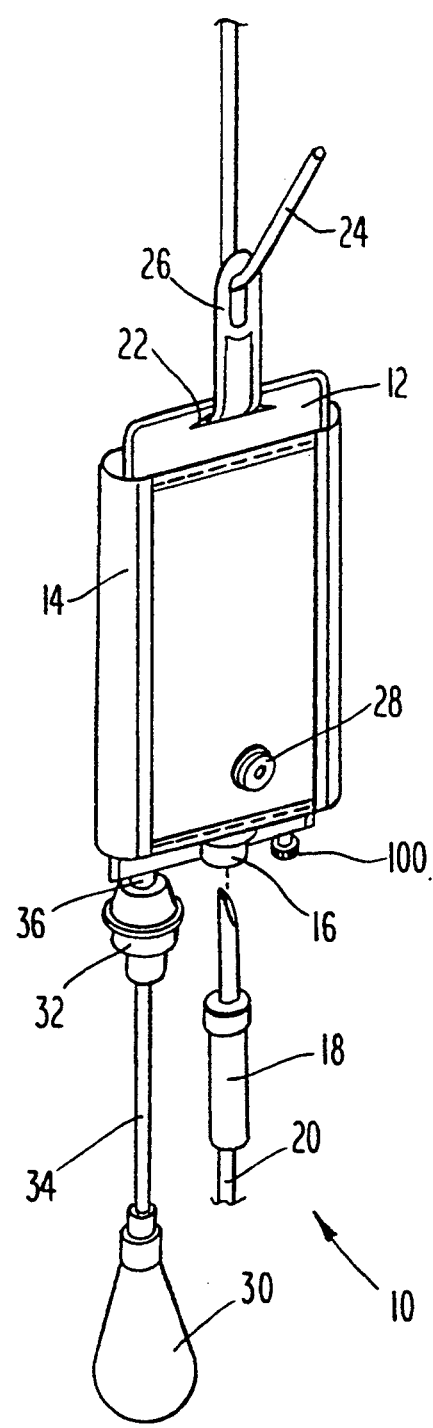
Fig. 1
Fig. 2

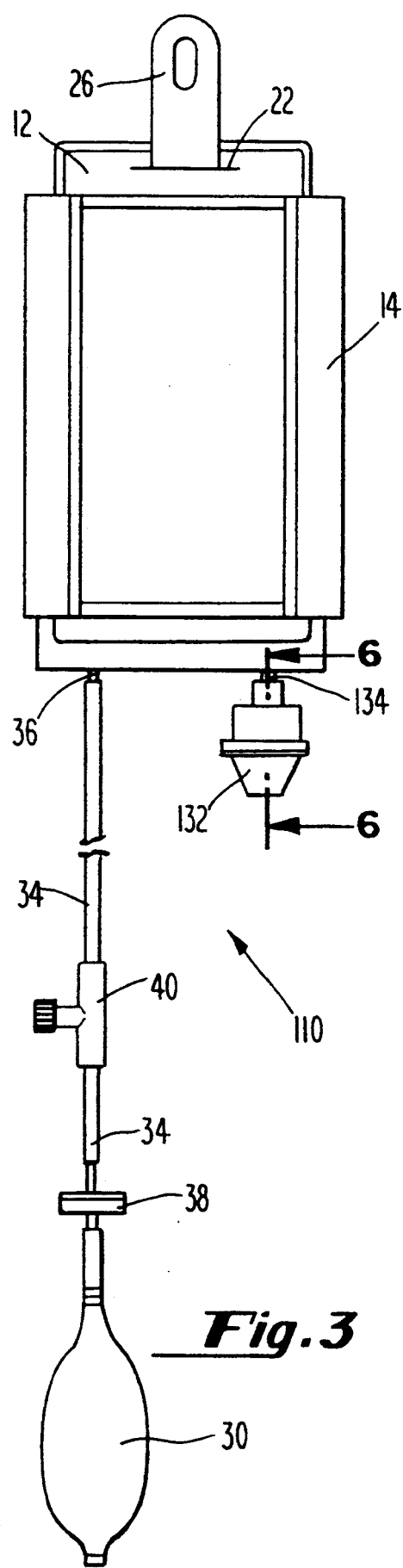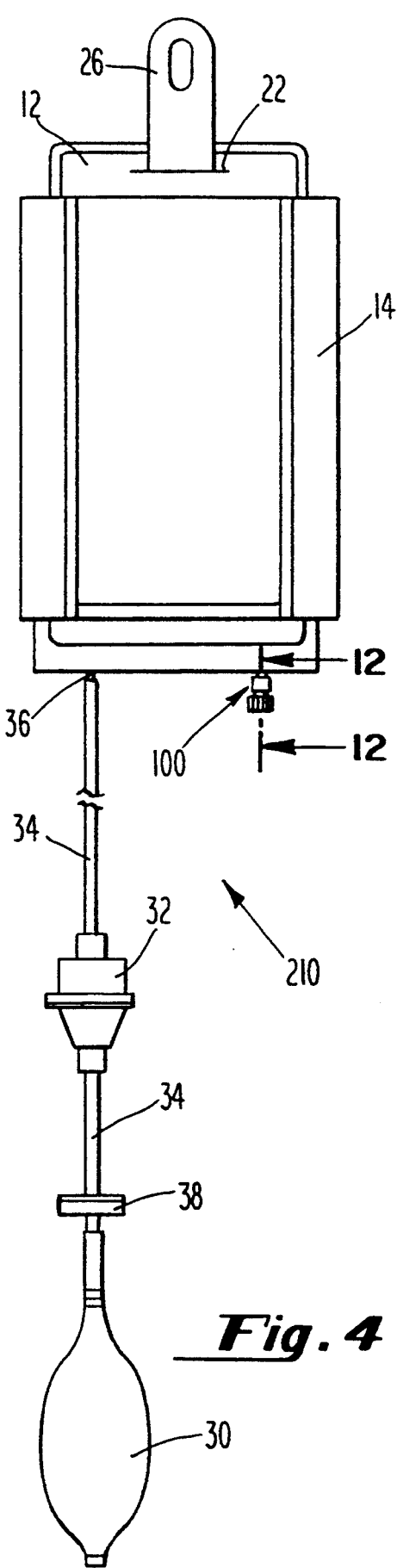

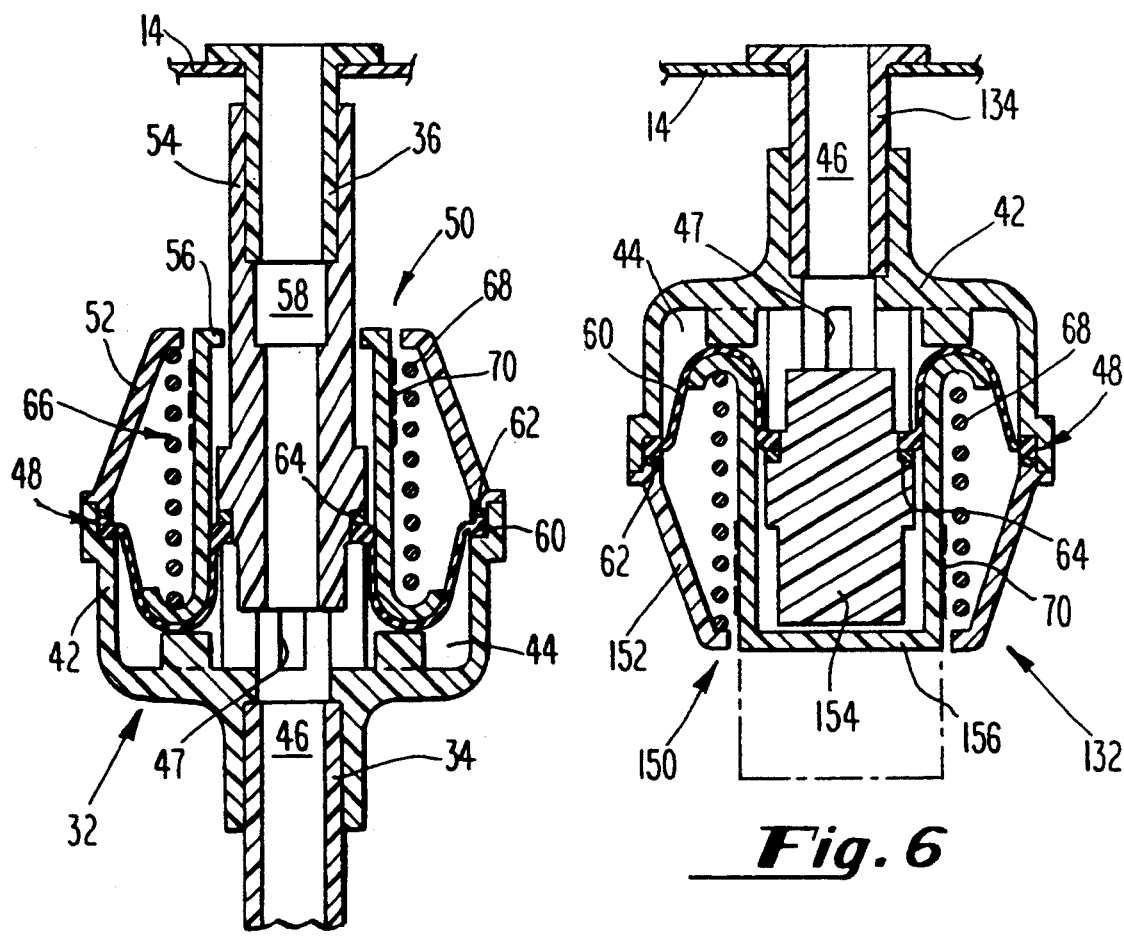
Fig. 5
Fig. 6
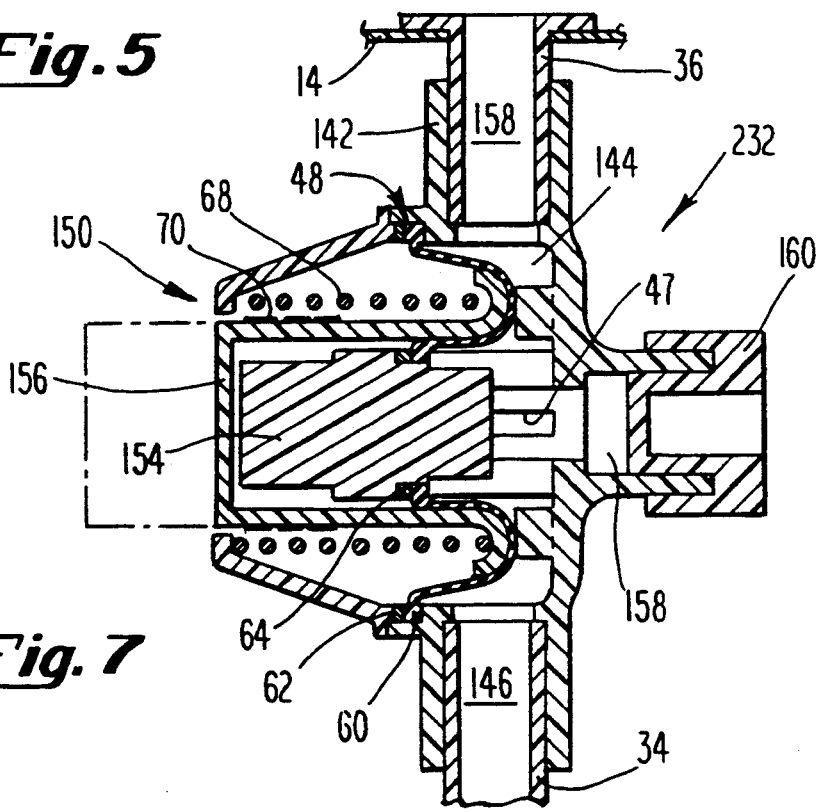
Fig. 7

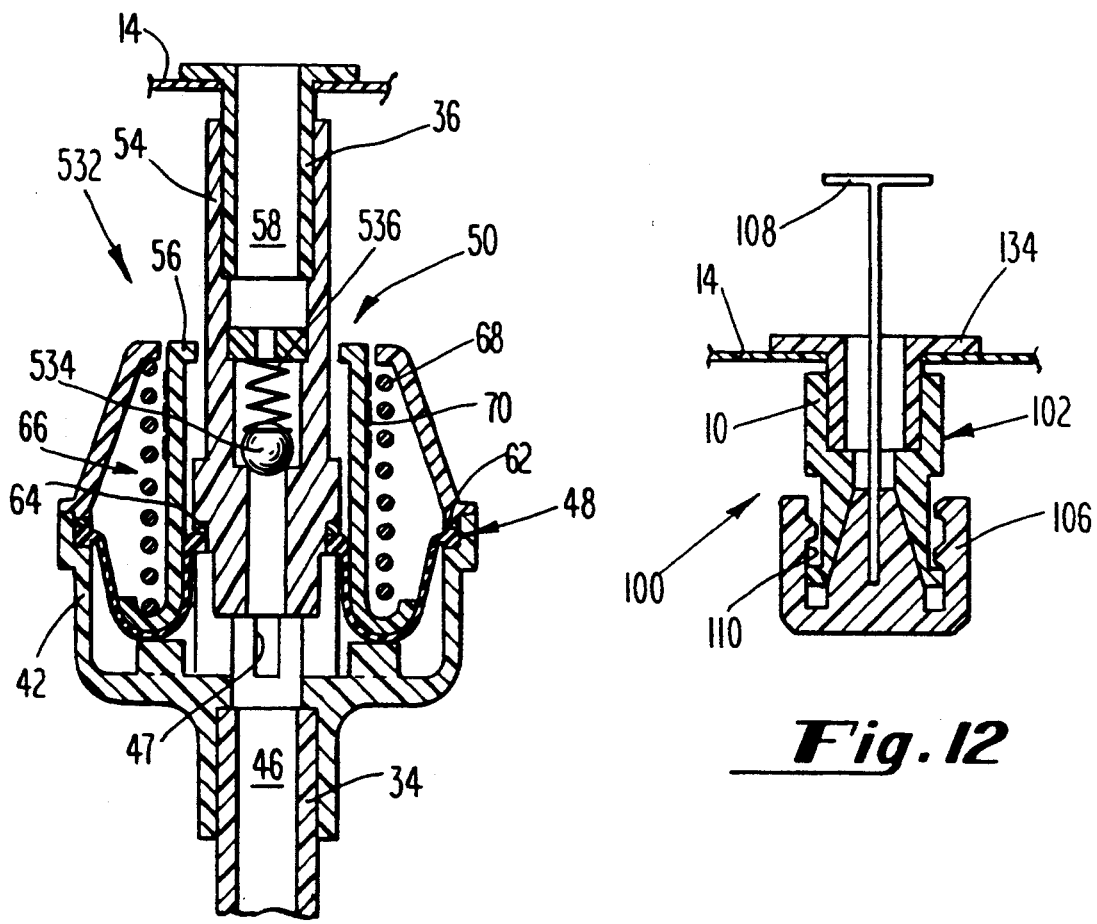
Fig. 11
Fig. 12
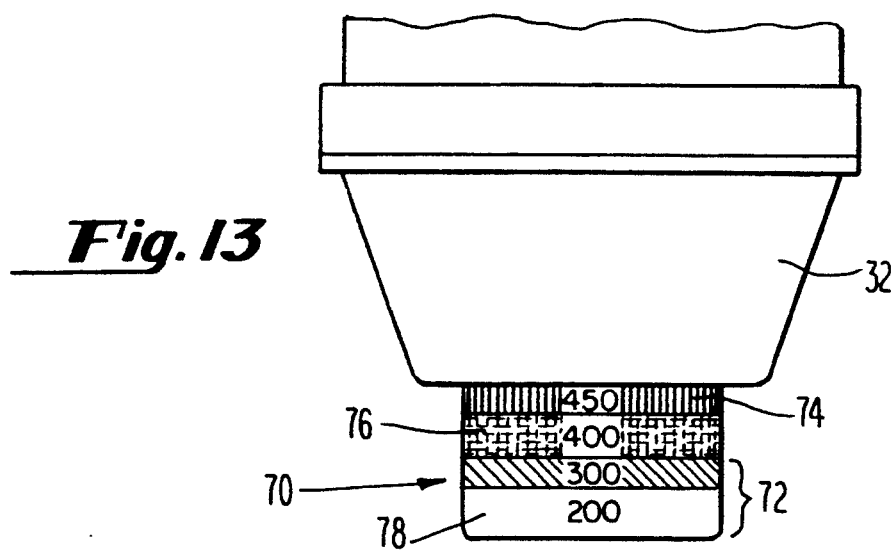
Fig. 13

PRESSURE GAUGE FOR REGULATING PRESSURE IN A DISPOSABLE PRESSURE CUFF

CROSS-REFERENCE TO RELATED APPLICATIONS

This application is a continuation-in-part application of copending application Ser. No. 415,068, filed Sep. 29, 1989, now U.S. Pat. No. 5,053,012 and is also related to copending applications Ser. No. 415,097, filed Sep. 29, 1989, now U.S. Pat. No. 5,053,011 Ser. No. 415,209, filed Sep. 29, 1989, now abandoned which are assigned to the same assignee and are incorporated herein by reference.

BACKGROUND OF THE INVENTION

1. Field of the Invention

The present invention is generally related to pressure infusion devices, and more particularly to disposable pressure cuffs having a pressure gauge.

2. Statement of the Prior Art

Liquids administered by intravenous injection, such as whole blood, plasma, saline and dextrose solutions, are typically supplied in disposable infusion bags which are most often made of a flexible, transparent plastic having an outlet port or delivery tube which is adapted to be punctured by a coupler of a recipient set. In use, the infusion bag is suspended above the patient and the liquid contained therein is permitted to flow by gravity into the patient's vein. There are many situations, particularly when the infusion bag is nearly empty or in cases of severe hemorrhage and shock, where the administration of fluid by gravity flow with conventionally employed infusion bags is unacceptably slow.

Various pressure infusion apparatus have been used in the past to overcome such problems of slow delivery. See, for example, U.S. Pat. No. 2,766,907, issued Oct. 16, 1956 to Wallace, Jr.; U.S. Pat. No. 3,153,414, issued Oct. 20, 1964 to Beall et al.; U.S. Pat. No. 4,090,514, issued May 23, 1978 to Hinck et al.; U.S. Pat. No. 4,507,116, issued Mar. 26, 1985 to Leibinsohn; and U.S. Pat. No. 4,735,613, issued Apr. 5, 1988 to Bellin et al. Such known pressure infusion apparatus characteristically comprises bladder means for maintaining a fluid under pressure, means forming a pocket with the bladder means for holding an infusion bag against the bladder means for pressurizing the infusion bag by transmission of pressure from the pressurized bladder means to the infusion bag, and pressurization means which is coupled to the bladder means for introducing a flow of the fluid into the bladder means and thereby pressurizing same.

With most pressure infusion apparatus, the bladder means is formed of an elastomeric material that is contained in an outer shell. For example, in U.S. Pat. No. 4,735,613 referenced above, Bellin et al. disclose a pressure bag that is formed of two sheets of plastic material fastened together along their edges. A fabric mesh is secured at its opposite sides to a fabric sheet and, thus, forms a pocket for holding an infusion bag and the pressure bag in engagement with each other. One problem that is presented by such conventionally-formed pressure infusion apparatus is the amount of visibility provided by the fabric mesh, for observing the infusion bag during administration of the fluid contained therein. Persons who would use such pressure infusion apparatus according to Bellin et al. would experience some difficulty in monitoring the progress of the administered fluid.

Other known pressure infusion apparatus, including those described in the patents noted above, provide better opportunities for observing the infusion bags during administration of the fluid contained therein by using a flexible, transparent sheet, which is attached to the bladder means for holding the infusion bag against the bladder means. However, various complicated means for joining such transparent sheets to the bladder means (e.g., sewn stitching or hook-and-pile means) in these known pressure infusion apparatus greatly increases their fabrication costs.

A suitable disposable pressure cuff is disclosed in the above-referenced copending application Ser. No. 415,097, filed Sep. 29, 1989, now U.S. Pat. No. 5,053,011. Various means for pressurizing such pressure cuffs are known in the prior art, but an inflation, or "squeeze" bulb is typically used as the pressurization means to minimize manufacturing costs. Providing a single-ended inflation bulb with check valves according to the above-referenced copending application Ser. No. 415,209, filed Sep. 29, 1989, now abandoned, further avoids problems of leakage which have been experienced by double-ended inflation bulbs of the prior art.

In order to provide fully-disposable pressure infusion systems, however, it is necessary to include adequate means for monitoring pressures within the bladder means. A simple tubular pressure gauge is shown and claimed in U.S. Pat. No. 4,735,613, referenced above. Nevertheless, the pressure gauge disclosed in U.S. Pat. No. 4,735,613 suffers from disadvantage of having to be installed within the bladder means. A more versatile pressure gauge, which has the capability of selective placement within the pressure infusion system by the user, would be desirable.

Additionally, it may be desirable to provide pressurized fluid to the bladder from a pressurized source. In such situations, hand-squeezing of the pressure bulb will be unnecessary, thereby freeing the medical technician to perform more important tasks.

SUMMARY OF THE INVENTION

Accordingly, it is a general object of this invention to provide a disposable pressure cuff which may be used in a pressure infusion system. It is a more particular object of this invention to provide improved gauge means for such disposable pressure cuffs, whereby pressurized fluid is automatically regulated without the need for inflation bulbs.

Another object of this invention is to provide disposable pressure cuffs which are inexpensively manufactured and safely, yet easily used.

Yet another object of this invention is to provide pressure regulating gauges for such disposable pressure cuffs.

Briefly, these and other objects according to the present invention are achieved in apparatus for regulating the pressure in a pressure infusion apparatus for controllably pressurizing infusion bags. The apparatus is a flow-through pressure gauge for indicating and regulating the pressures within such infusion bags between minimum and maximum desirable pressures. Such apparatus is shown to include conduit for transmitting fluid from a fluid source and a gauge, coupled between the fluid source and the bladder portion of the pressure infusion device by such conduit. The gauge receives pressurized fluid from the source, provides fluid to the bladder, indicates a range of fluid pressures in the bladder and maintains the pressure of fluid in the bladder between minimum and maximum pressures. In a preferred embodiment the gauge includes a first housing for receiving a flow of fluid under pressure, which first housing includes a body forming a chamber having an inlet and outlet and a first member projecting from the body. The gauge also includes a diaphragm for sealing the chamber and a second housing for enclosing the chamber. The second housing includes a second member telescopingly coupled to the first member for movement thereupon to indicate a range of pressures of fluid in the bladder. A first valve is formed between the first and second housings, for permitting the passage of fluid through the chamber and into the bladder when the fluid pressure exceeds a minimum pressure. A second valve is formed between the first and second housings, for preventing the passage of fluid through the chamber and into the bladder when the fluid pressure exceeds a maximum pressure.

BRIEF DESCRIPTION OF THE DRAWINGS

These and other objects, advantages and novel features according to the present invention will become apparent from the following detailed description of the preferred embodiment, when considered in conjunction with the accompanying drawings wherein:

FIG. 1 generally depicts disposable pressure infusion apparatus;

FIG. 2 shows a disposable pressure cuff having one embodiment of a flow-through pressure gauge in pressure infusion apparatus;

FIG. 3 shows a disposable pressure cuff having a flow-through pressure gauge in pressure infusion apparatus according to a second embodiment;

FIG. 4 shows a disposable pressure cuff having a flow-through pressure gauge in pressure infusion apparatus according to a third embodiment;

FIG. 5 is a sectional view of the flow-through pressure gauge shown in FIG. 2, taken along the lines 5—5;

FIG. 6 is a sectional view of the flow-through pressure gauge shown in FIG. 3, taken along the lines 6—6;

FIG. 7 is a sectional view of an alternative flow-through pressure gauge;

FIG. 11 is a sectional view of the flow-through pressure gauge shown in FIG. 5, further incorporating pressure relief means;

FIG. 12 is a sectional view of the dump valve shown in FIG. 4, taken along the lines 12—12;

FIG. 13 illustrates the preferred means for indicating pressures measured by the flow-through pressure gauge;

DETAILED DESCRIPTION OF THE INVENTION

Figure 8:
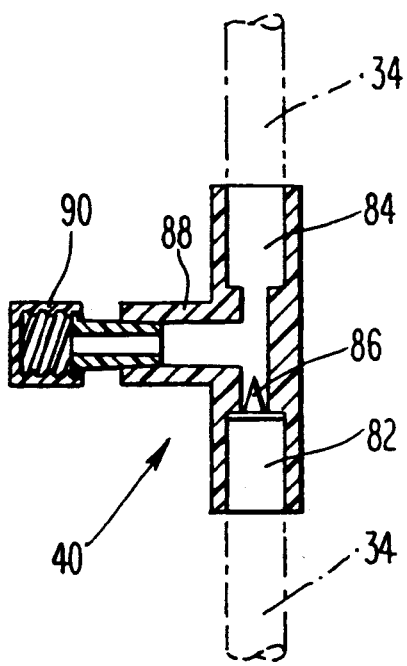
FIG. 8 is a sectional view of the combination dump valve-check valve shown in FIG. 2, taken along the lines 8—8.

Referring now to the drawings, wherein identical numbers designate like or corresponding parts throughout the several views, there is shown in FIG. 1 pressure infusion apparatus 10 for use in pressurizing an infusion bag 12 with a disposable pressure cuff 14.

As is well known, the typical infusion bag 12 is fitted with an outlet port 16 adapted to be punctured by a coupler 18 of a recipient set. Liquids, such as whole blood, plasma, saline or dextrose solutions, contained in the infusion bag 12 are supplied to the patient through intravenous injection by way of a delivery tube 20. The infusion bag 12 also conventionally includes a slit 22 for hanging the pressure infusion apparatus 10 from a hook 24, by way of a hanger 26 that is threaded through such slit 22. For the purpose of injecting a drug into the administered liquid, the infusion bag 12 may also be fitted with an injection port 28.

The pressure infusion apparatus 10, as is conventional, includes bladder means for maintaining a fluid under pressure and means for pumping a flow of the fluid into the bladder means. As shown in FIG. 1, the pumping means comprises an inflation bulb 30 which is coupled to a pressure gauge 32 by way of flexible tubing 34. The pressure gauge 32, in turn, couples to the bladder means by way of a pressurization port 36. Further information regarding the pressure cuff 14, and a preferred method of fabricating same, may be found in copending application Ser. No. 415,097, filed Sep. 29, 1989, now U.S. Pat. No. 5,053,011, and information regarding check valves useful with the pressure infusion apparatus may be found in copending application Ser. No. 415,209, filed Sep. 29, 1989, now abandoned, each of which is assigned to the assignee of the present invention and incorporated herein by reference.

As is shown in FIG. 2, the pressure infusion apparatus 10 according to one embodiment includes a pressure cuff 14, of the type having a bladder for maintaining a fluid under pressure and a pocket for holding the infusion bag 12 in contact with the bladder, and means for introducing a flow of the fluid into the bladder.

Figure 14:
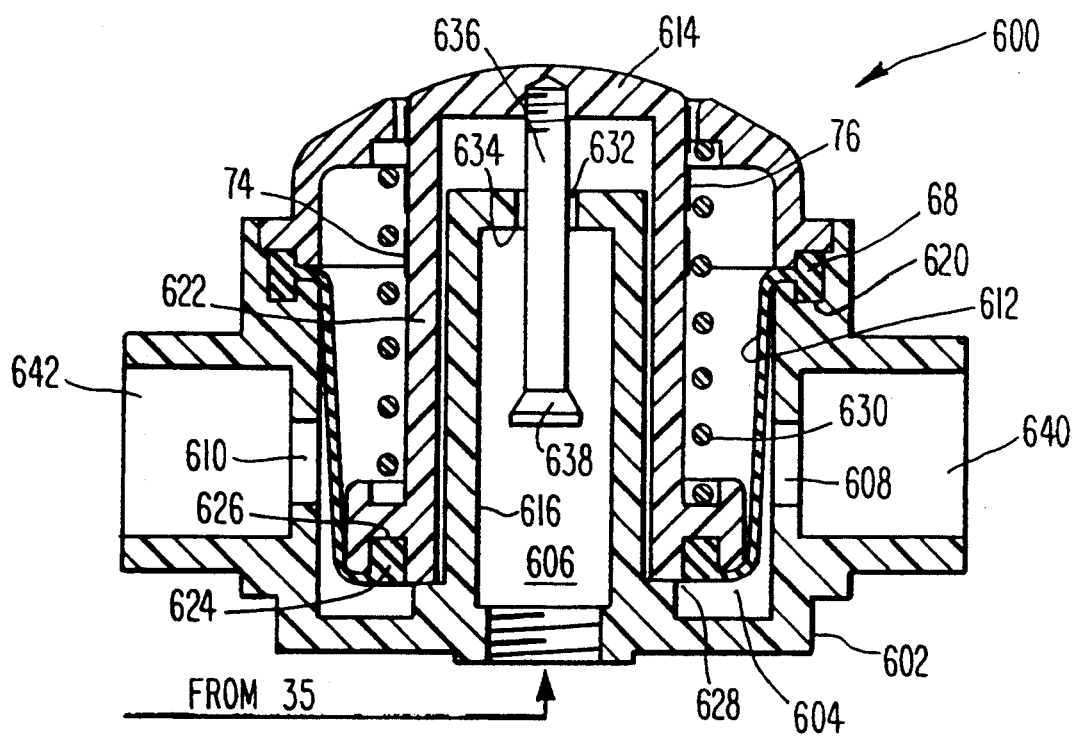
FIG. 14 is the preferred embodiment of the flow-through pressure gauge shown in FIG. 5 according to the present invention.
Figure 15:
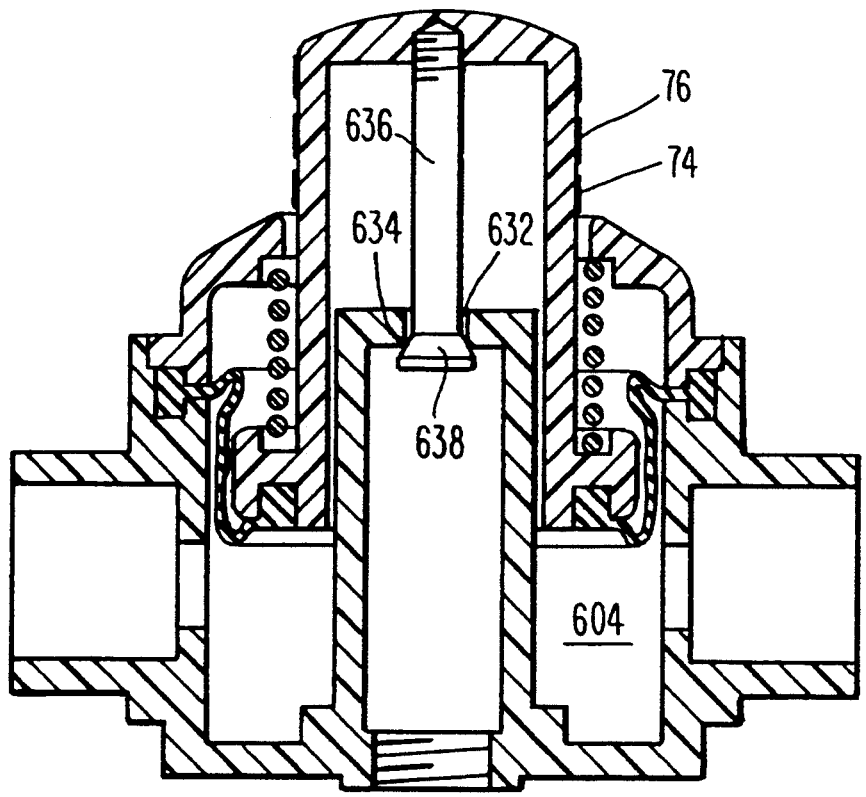
FIG. 15 is a section view identical to FIG. 14, except the second member is depicted in an extended position.

The fluid typically used is air, but other fluids such as nitrogen, carbon dioxide and Freon® may be equally used. It may also be desired to provide any one of these fluids from a pressurized source 35. The embodiment of the present invention depicted in FIGS. 14 and 15 is particularly adaptable for such an arrangement. As will be described in connection with those figures, the pressure valve acts to automatically regulate the pressure in the bladder between minimum and maximum pressure values.

Like the pressure infusion apparatus 10 of FIG. 1, the flow introducing means according to FIG. 2 also comprises an inflation bulb 30 which is coupled to a flow-through pressure gauge 32 by way of flexible tubing 34. The inflation bulb 30 is, as is evident from FIG. 2, of the double-ended type that includes a check valve 38 coupled to one end thereof. Check valve 38 is further connected by a length of the flexible tubing 34 to a dump valve 40 which is used to release pressure from the bladder means of the pressure cuff 14 as necessary. The dump valve 40 is then coupled to the flow-through pressure gauge 32 by another length of the flexible tubing 34.

Referring for the moment to FIG. 5, the details of one embodiment of flow-through pressure gauge 32 will now be explained. Pressure gauge 32 according to this embodiment generally comprises means for indicating a range of pressures within the bladder means of pressure cuff 14 which includes first housing means 42 forming a chamber 44 and an inlet 46 to the chamber 44, diaphragm means 48 for sealing the chamber 44, and telescoping means 50, mounted upon the diaphragm means 48 and adapted to be moved thereby to indicate a range of pressures within bladder means of pressure cuff 14, and second housing means 52 that encloses the chamber 44. Telescoping means 50 generally comprises a first member 54 which is coupled to the first housing means 42, and a second member 56, telescopingly coupled to first member 54 for movement thereon. Any pressurizing fluid from the flow introducing means enters through the inlet 46, passes through inlet holes 47 for passage into the chamber 44, and additionally passes through the tubular first member 54 to outlet 58. Accordingly, first and second members 54, 56 of telescoping means 50 indicate a range of pressures not only within the bladder means, but also within the flow of fluid through the chamber 44.

Pressure gauge 32 further comprises an outlet 58 from the chamber 44, such that the flow of fluid through pressure gauge 32 defines an axis A between its inlet 46 and the outlet 58. As shown in FIG. 5, therefore, it can be seen that telescoping means 50 will be adapted for movement by diaphragm means 48 in an axial direction relative to the flow of fluid between inlet 46 and outlet 58. The diaphragm means 48 generally comprises a resilient annulus 60 which covers the chamber 44, and a pair of rings 62 and 64 for retaining the annulus 60 in place. Ring 62 retains the resilient annulus 60 at its outside diameter, and ring 64 retains the resilient annulus 60 at its inside diameter.

In order to move the telescoping means 50, the pressure gauge 32 further comprises means 66 for biasing the diaphragm means 48 against the range of pressures expected within the bladder means of pressure cuff 14. That is, second housing means 52 itself forms a third member which retains spring means 68. The third member 52 is disposed coaxially about first and second members 54, 56 and is coupled to the first housing means 42 for substantially preventing movement of diaphragm means 48 below a predetermined pressure of the flow of pressurizing fluid. Preferably, the biasing means 66 comprises spring means such as the coil spring 68 that is mounted between the second member 56 and the third member 52. Referring for the moment also to FIG. 1, it can be seen that pressure gauge 32 is coupled between flow introducing means 30 and the pressure cuff 14 by coupling the inlet 46 to the flexible tubing 34 and the outlet 58 to the pressurization port 36.

When the bladder means of pressure cuff 14 is thereafter pressurized, pressure within the chamber 44 is communicated to the second member 56 through the elasticity of diaphragm means 48. An indicating means 70 placed on the second member 56 (as is shown in greater detail in FIG. 13) becomes exposed when diaphragm means 48 moves the second member 56 above second housing means 52. That is, the coil spring 68 is selected to have a preset load such that the second member 56 will not begin to move until the pressure cuff 14 is at the predetermined pressure (e.g., about 100 mm Hg). As the pressure increases above the predetermined minimum, more and more of the indicating means 70 will become exposed at a proportionate rate. Such displacement of the second member 56 to further expose the indicating means 70 is generally a function of certain tensile characteristics of diaphragm means 48, as well as the rate (i.e., force/distance) of the coil spring 68. In the embodiment shown in FIG. 13, for example, the second member 56 will move at a constant linear rate of about 0.15 inches per 100 mm Hg pressure for a total of about 0.6 inches across a range of from 100 mm Hg to 500 mm Hg.

A disposable pressure cuff 14 with a pressure gauge 32 in pressure infusion apparatus 110 according to a second embodiment is shown in FIG. 3. As in the case of the pressure infusion apparatus 10 illustrated in FIG. 2, such pressure infusion apparatus 110 generally comprises a pressure cuff 14 with a bladder for maintaining a fluid under pressure and a pocket for holding the infusion bag 12 in contact with the bladder, and means for introducing a flow of the fluid into the bladder comprising a double-ended inflation bulb 30. The fluid typically used is air, but other fluids such as nitrogen, carbon dioxide and Freon ® may be introduced with automatic pumps or pressurized bottles. A check valve 38 is also connected to the inflation bulb 30, and is further connected by a length of the flexible tubing 34 to a dump valve 40 in a similar manner as in the pressure infusion apparatus 10 shown in FIG. 2. The dump valve 40 is then coupled to the pressure cuff 14 by another length of the flexible tubing 34.

Unlike the previous embodiment, the pressure infusion apparatus 110 includes an "end-of-circuit" pressure gauge 132 that is attached to the pressure cuff 14 via output port 134. Referring now to FIG. 6, the details of the end-of-circuit pressure gauge 132 will now be explained. Such pressure gauge 132 generally comprises first housing means 42 forming a chamber 44 and an inlet 46 to the chamber 44, diaphragm means 48 sealing the chamber 44, telescoping means 150 mounted upon the diaphragm means 48 adapted for movement thereby, and second housing means 152 that encloses chamber 144. Telescoping means 150 generally comprises a first member 154 which is coupled to the first housing means 42, and a second member 156, telescopingly coupled to the first member 154 and moved thereupon. First and second members 154 and 156 of such telescoping means 150 also indicate the range of pressures within the bladder means by extension of such second member 156 through second housing means 152. However, second member 156 comprises a solid member with no outlet which would permit the pressurizing fluid to flow through. In all other respects, the end-of-circuit pressure gauge is like the pressure gauge 32 shown in FIG. 5. Pressurizing fluids from the bladder means of pressure cuff 14 in this embodiment enters through the inlet 46 and passes through inlet holes 47 into the chamber 44.

Flow-through pressure gauges also include those having their telescoping means adapted for movement by the diaphragm means in a transverse direction with respect to the flow of fluid between their inlet and outlet. That is, and referring now to FIG. 7, a flow-through pressure gauge 232 so adapted generally comprises first housing means 142 which forms a chamber 144, an inlet 146 to chamber 144, and an outlet 158 from chamber 144, diaphragm means 48 sealing chamber 144, telescoping means 150 which is mounted upon the diaphragm means 48 adapted for movement thereby to indicate a range of pressures within bladder means of pressure cuff 14, and second housing means 252 enclosing chamber 44. Telescoping means 150 also generally comprises a first member 154 that is coupled to the first housing means 142, and a second member 156, telescopingly coupled to the first member 154 to be moved thereupon. Pressurizing fluid from flow introducing means enters through inlet 146, passes through inlet holes 47 for passage into the chamber 144, and additionally passes from chamber 144 through outlet 158. Accordingly, the first and second members 154, 156 of telescoping means 50 indicate a range of pressures not only within the bladder means of pressure cuff 14, but also within the flow of fluid through the chamber 144.

In contradistinction to the other pressure gauges 32, 132 which have been previously described, the pressure gauge 232 shown in FIG. 7 also comprises another outlet 158 that is normally closed by dump valve means 160 for releasing built-up pressures within the pressure infusion apparatus. These dump valve means 160 preferably comprise conventional "luer" valves as will be discussed in greater detail herein below.

Referring again to FIG. 2, it should be noted that the pressure infusion apparatus 10 which is shown therein includes a dump valve 40. As shown in FIG. 8, such dump valve 40 generally comprises a valve body 80 having an inlet 82 coupled to a length of flexible tubing 34 and an outlet 84 coupled to another length of flexible tubing 34. The inlet 82 also comprises a "duckbill" type check valve 86, although other forms of check valves are as suitable without departing from the scope of this invention. An extension 88 of the valve body 80 also includes a luer valve 90, which is adapted to release built-up pressures within the pressure infusion apparatus in a well known manner.

Figure 9:
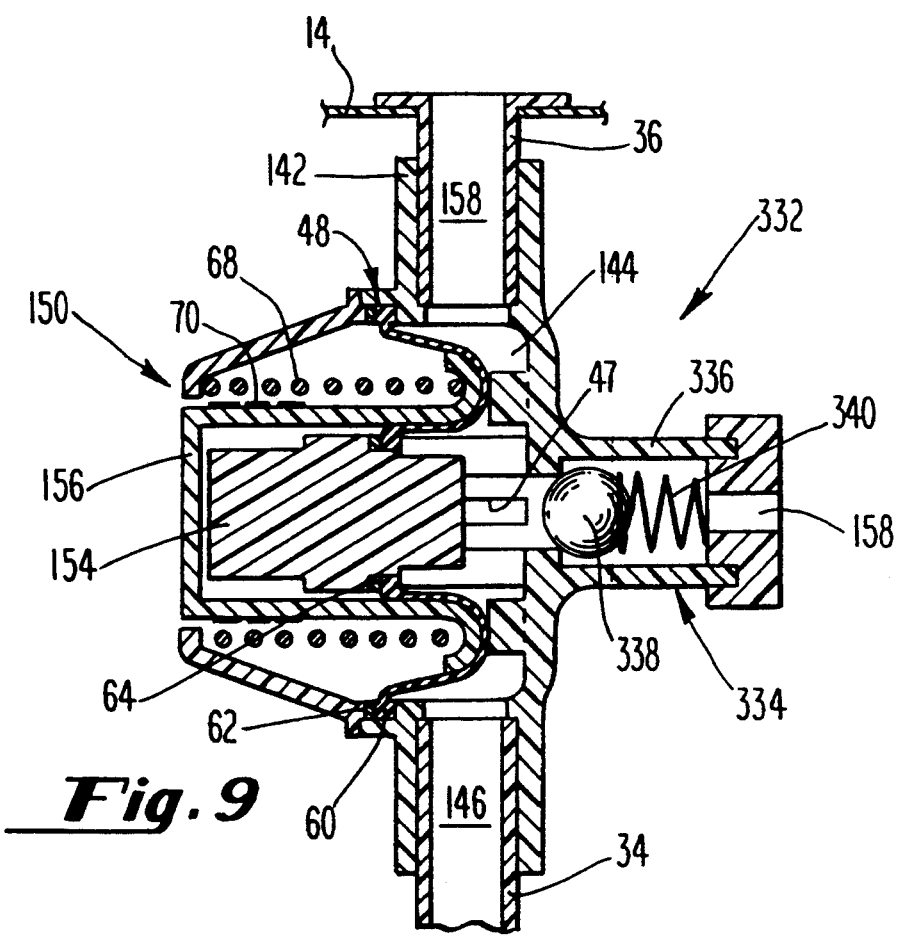
FIG. 9 is a sectional view of the flow-through pressure gauge shown in FIG. 7, further incorporating pressure relief means according.

A sectional view of the flow-through pressure gauge shown in FIG. 6 which incorporates pressure relief means is shown in FIG. 9. As shown therein, a pressure gauge 332 (which is similar in most respects to pressure gauge 232) further comprises pressure relief means 334 including an extension 336 of the first housing means 142 having another outlet 158 which permits a release of pressure from the fluid above a predetermined maximum pressure. The outlet 158 within the pressure relief means 334 is normally closed by a ball valve 338, which is controlled by a spring 340. Various maximum pressures are adapted for selection by installing a spring 340 with a particular force.

Figure 10:
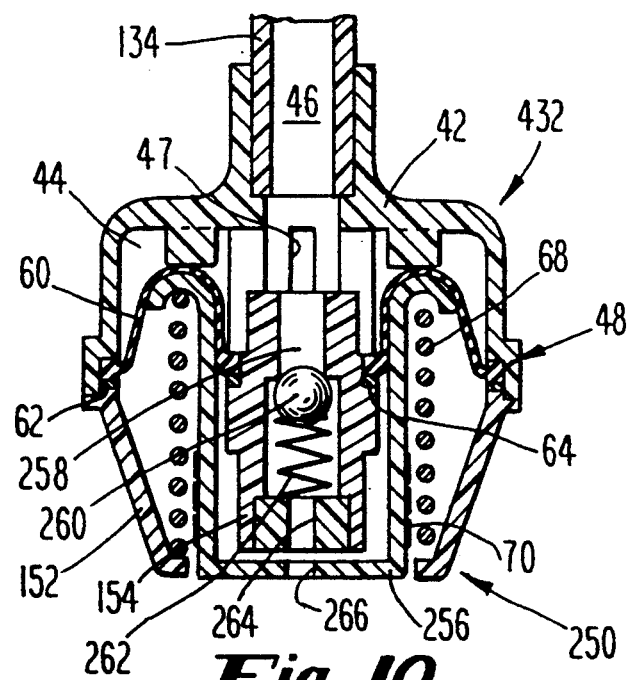
FIG. 10 is a sectional view of the flow-through pressure gauge shown in FIG. 6, further incorporating pressure relief means.

The flow-through pressure gauge 132 shown in FIG. 6 may also incorporate a pressure relief means as shown in FIG. 10. A pressure gauge 432 according to this embodiment is similar in most respects to pressure gauge 132 with the exception that it includes a telescoping means 250 which has a first member 254 coupled to the first housing means 42, and a second member 256 that is adapted for relieving pressure within the chamber 44. Such first member 254 comprises passage 258 that is in communication with the chamber 44, a ball valve 260 that is controlled by a spring 262, and a pressure relief port 264. Such spring is also selected to have a bias force corresponding to the particular predetermined maximum pressure which is desirable with the pressure infusion apparatus. When such predetermined maximum pressure is exceeded, the force of spring 262 is overcome and the ball valve 260 is displaced to open passage 258. Relief of those excessive pressures is, thereafter, facilitated by passage through a pressure relief port 266 in the second member 256.

Yet another embodiment of a flow-through pressure gauge 532 is shown in FIG. 11. Such flow-through pressure gauge 532 also incorporates regulating means for regulating minimum pressures delivered through pressure gauges of the type shown in FIG. 5. The gauge 532 is also similar in most respects to pressure gauge 32, and has first and second members 54, 56. However, first member 54 also includes a ball valve 534 which is controlled by a spring 536. When a flow of the fluid is set up by the flow introducing means through the inlet 46, such flow will not be passed through outlet 58 until a pressure within chamber 44 reaches a predetermined minimum. That is, the ball valve 534 will normally be closed by the selected force of the spring 536. After the flow introducing means increases the pressure of chamber 44 to the predetermined minimum, however, such pressure overcomes forces of the spring 536, displaces the ball valve 534 to open outlet 58, and thereby facilitates the bladder means of pressure cuff 14 to be pressurized. It can be seen that telescoping means 50 operates in the manner described with reference to FIG. 5, notwithstanding the fact that pressures within chamber 44 will not be transmitted to the pressure cuff 14 until the ball valve 534 is displaced.

Referring now to FIG. 4, there is shown a yet another disposable pressure cuff 14 having a flow-through pressure gauge 32 in pressure infusion apparatus 210 in accordance with a third embodiment. As in each of the previous cases, the pressure infusion apparatus 210 generally comprises a pressure cuff 14 having a bladder which maintains a fluid under pressure and a pocket for holding the infusion bag 12 in contact with the bladder, and means for introducing a flow of the fluid into the bladder comprising a double-ended inflation bulb 30. A single-ended inflation bulb as disclosed in copending application Ser. No. 415,209, filed Sep. 29, 1989, now abandoned may alternatively be used. The fluid typically used is air, but other fluids such as nitrogen, carbon dioxide and Freon ® may be introduced with automatic pumps or pressurized bottles. A check valve 38 is also connected to the inflation bulb 30, and is also connected by a length of the flexible tubing 34 to pressure gauge 32 or any of the other pressure gauges shown hereinbefore. Pressure infusion apparatus 210 also comprises dump valve means 100.

As shown in FIG. 12, the dump valve means 100 comprises luer valve means 102 having a neck portion 104 that is coupled to the outlet port 134 and a cap 106 that includes a retaining means 108. Any excessive pressure within the bladder means of pressure cuff 14 may be manually relieved by using luer valve means 102 in a conventional manner. That is, as the cap 106 is unscrewed from the thread 110 of neck portion 104, pressures are relieved through outlet port 134. In order to prevent cap 106 from being unscrewed, such cap 106 is attached to the retaining means 108 that is adapted not to pass completely through the outlet port 134.

Referring now to FIG. 13, details of the indicating means 70 will now be described. In a presently preferred embodiment of the invention, such indicating means 70 generally comprises a first band 72 which surrounds the indicating second members at a selected upstream perimeter thereof, and a final band 74 which surrounds the second members at a selected downstream perimeter thereof. First band 72 is adapted to indicate the predetermined minimum pressure, and final band 74 is adapted to indicate the predetermined maximum pressure. One or more additional bands 76, each of which surrounds the indicating second member at a respective perimeter between the selected upstream perimeter and the selected downstream perimeter, may be used to indicate pressures between the predetermined minimum pressure and the predetermined maximum pressure. As shown in FIG. 13, the final band 74 preferably comprises a red-colored band which indicates the dangers of exceeding such pressures, while the first band 72 preferably comprises a green-colored band which indicates the safety of operating at such pressures. One of the additional bands 76 preferably comprises a yellow-colored band which indicates the approach of dangerous pressures. An uncolored band 78 may also be used for indicating pressures below the safe level. Numbers may be used to assist in the ready reading of such pressure levels.

Referring now to FIG. 14, the details of the preferred embodiment of the present invention will be explained. Like numerals have been used on like components where possible. Pressure gauge 600 according to this preferred embodiment generally includes a means for indicating a range of pressures within the bladder of pressure cuff 14 (FIG. 2). Fluid passed through gauge 600 typically will be air, but other fluids such as nitrogen, carbon dioxide and Freon ® may be used. Fluid is introduced from fluid source 35 (FIG. 2), which may be a hand pump, an automatic pump or a pressurized bottle. Gauge 600 includes first housing means 602 forming a chamber 604 having an inlet 606 and two outlets 608 and 610. Diaphragm 612 seals chamber 604 and telescoping means 614 is mounted upon diaphragm 612 and adapted to be moved thereby to indicate a range of pressures within the bladder. Telescoping means 614 also serves as a second housing that also serves to enclose chamber 604.

Gauge 600, when incorporated into the pressure infusion system shown in FIG. 2, is coupled between fluid source 35 and the bladder of pressure cuff 14 by conduit 34. Gauge 600 receives pressurized fluid from source 35 and provides fluid to the bladder. Gauge 600 also indicates a range of fluid pressures in the bladder and maintains the pressure of fluid in the bladder between minimum and maximum pressures. Thereby, fluid pressure in the bladder is automatically regulated.

First housing member 602 receives fluid under pressure from source 35 at inlet 606. As shown in FIG. 14, inlet 606 is provided with threads for the attachment of conduit or tubing. Member 602 includes a body which defines a portion of chamber 604. A first member 616 projects from the body of first housing 602. Diaphragm 612 for sealing chamber 604 is connected to housing 602 by positioning flanged end 618 in slot 620. Slot 620 is covered by cap member 621. Second housing 614 includes a second member 622 telescopingly coupled to first member 616 for movement thereupon to indicate a range of fluid pressures by indicia 74 and 76. Diaphragm 612 is connected to second housing 614 by positioning flanged end 624 in slot 626.

A first valve 628 is formed between first housing 602 and second housing 614, for permitting the passage of fluid through chamber 604 when the pressure of fluid exceeds a minimum pressure or cracking pressure. First valve 628 is operative in relation to biasing spring 630. Spring 630 serves to bias the second housing against the first housing. Minimum or cracking pressure is dependent on the force required to counteract the force exerted by spring 630.

A second valve 632 is formed between first housing 602 and second housing 614, for preventing the passage of fluid through chamber 604 when fluid pressure exceeds a maximum pressure. Valve 632 includes a valve seat 634 formed on body projection 616. Second housing 614 includes piston or valve stem 636 which extends through valve seat 634 and which has a flared end 638 formed at its distal end. As fluid pressure increases, second housing 614 will move telescopically in relation to projection 616 until flared end 638 contacts valve seat 634, as shown in FIG. 15. Upon such contact, fluid is prevented from passing into chamber 604, thereby preventing the pressure in the bladder from increasing.

By selecting spring 630 to exhibit a particular force and by selecting a particular length for piston 636, gauge 600 will automatically maintain the pressure in the bladder between desired minimum and maximum pressures. It is within the scope of the invention to provide valve stem 636 with an externally adjustable structure. For example, the end of valve stem 636 is shown as threaded. If such threads were extended along the valve stem and if the valve stem extended through second housing 614, one could increase or decrease the maximum pressure in the bladder by turning the valve stem. Thus, the maximum bladder pressure could be manually adjusted.

Pressure gauge 600 includes two outlets 640 and 642 for connection to two pressure infusion devices. Consequently, bladder pressure can be regulated for two pressure infusion devices simultaneously.

Obviously, many modifications and variations are possible in light of the foregoing teachings. It should be understood that, within the scope of the appended claims, the present invention may be practiced otherwise than is specifically described herein.

What is claimed as our invention is:

1. Apparatus for regulating fluid pressure in a pressure infusion device having an infusion bag, a bladder for containing a fluid under pressure, and a pocket holding the infusion bag in contact with the bladder, wherein said fluid under pressure is supplied by a fluid source, said apparatus comprising: conduit for transmitting fluid from said fluid source; and gauge means, coupled between said fluid source and said bladder by said conduit, for receiving said fluid under pressure from said source and providing said fluid to said bladder, for indicating a range of fluid pressures therein and for maintaining the pressure of fluid in said bladder between minimum and maximum pressures, whereby the pressure of fluid in said bladder is automatically regulated, said gauge means comprising:

first housing means for receiving a flow of said fluid under pressure, said first housing means comprising a body forming a chamber having an inlet and an outlet and a first member projecting from said body;

diaphragm means for sealing said chamber;

second housing means for enclosing said chamber, said second housing means comprising a second member telescopingly coupled to said first member for movement thereupon to indicate a range of pressures of said flow of fluid through said chamber, wherein said diaphragm means is connected between said first housing means and said second housing means;

a first valve means, formed between said first housing means and said second housing means, for permitting the passage of fluid through said chamber when the pressure of fluid exceeds a minimum pressure; and a second valve means, formed between said first housing means and said second housing means, for preventing the passage of fluid through said chamber when the pressure of said fluid exceeds a maximum pressure.

2. The apparatus of claim 1 wherein said first valve means comprises a first valve seat formed on said body and a spring, connected between said first and second housing means, for biasing said second housing means against said first valve seat.

3. The apparatus of claim 1, wherein said chamber further comprises a second outlet, wherein said gauge means is connectable to a second pressure infusion device.

4. The apparatus of claim 1, wherein said first and second members are coaxially aligned.

5. The apparatus of claim 1, wherein said diaphragm means comprises:
a resilient annulus covering said chamber; and
first and second slots retaining said resilient annulus, said first slot formed in said first housing and said second slot formed in said second housing.

6. The apparatus of claim 1, wherein said second valve means comprises a second valve seat formed on said body and wherein said second housing means comprises a piston having a flared end, wherein said flared end is biased against said second valve seat in relation to the pressure of said fluid.

7. The apparatus of claim 6, wherein said second valve seat is formed around said inlet.

* * * * *